United States Patent
Ariyoshi

(10) Patent No.: US 8,803,959 B2
(45) Date of Patent: Aug. 12, 2014

(54) POLARIZATION OBSERVATION DEVICE

(71) Applicant: Olympus Medical Systems Corp., Tokyo (JP)

(72) Inventor: Daiki Ariyoshi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/913,940

(22) Filed: Jun. 10, 2013

(65) Prior Publication Data

US 2013/0314519 A1    Nov. 28, 2013

Related U.S. Application Data

(63) Continuation of application No. PCT/JP2012/075772, filed on Oct. 4, 2012.

(30) Foreign Application Priority Data

Nov. 29, 2011    (JP) ................................. 2011-260776

(51) Int. Cl.
*H04N 5/225*    (2006.01)
(52) U.S. Cl.
USPC ............................................................ 348/68
(58) Field of Classification Search
USPC ............................................................ 348/68
See application file for complete search history.

(56) References Cited

U.S. PATENT DOCUMENTS

| | | | |
|---|---|---|---|
| 5,838,653 A * | 11/1998 | Fan et al. .................... | 369/275.1 |
| 6,464,633 B1 | 10/2002 | Hosoda et al. | |
| 2003/0040668 A1 * | 2/2003 | Kaneko et al. ............... | 600/407 |
| 2009/0225156 A1 * | 9/2009 | Akiyama et al. ............. | 348/68 |
| 2009/0306478 A1 * | 12/2009 | Mizuyoshi .................... | 600/178 |
| 2012/0307128 A1 * | 12/2012 | Vorovitchik .................. | 348/336 |

FOREIGN PATENT DOCUMENTS

| | | |
|---|---|---|
| EP | 1 079 255 A2 | 2/2001 |
| EP | 2 100 551 A1 | 9/2009 |
| JP | 2001-235686 A | 8/2001 |
| JP | 2003-047588 A | 2/2003 |
| JP | 2007-143580 A | 6/2007 |
| JP | 2009-213649 A | 9/2009 |
| JP | 2010-125284 A | 6/2010 |

* cited by examiner

*Primary Examiner* — Mehrdad Dastouri
*Assistant Examiner* — Mohammed Rahaman
(74) *Attorney, Agent, or Firm* — Scully, Scott, Murphy & Presser, P.C.

(57) ABSTRACT

The invention includes: a light source section generating illumination lights in plural different wavelength bands; a first polarization element polarizing, in a first direction, a light in a first wavelength band among the illumination lights or returned lights from a subject; a second polarization element polarizing, in a second direction, a light in a second wavelength band among the illumination lights or returned lights; an image pickup device generating a first image pickup signal based on polarized light from the first polarization element and a second image pickup signal based on polarized light from the second polarization element; and an image processing section that compares intensities of the first and second image pickup signals, calculates the first or second direction corresponding to the image pickup signal having a higher intensity, as a polarization direction of the subject, and outputs a signal for displaying information on the polarization direction.

3 Claims, 7 Drawing Sheets

POLARIZATION OBSERVATION DEVICE

CROSS REFERENCE TO RELATED APPLICATION

This application is a continuation application of PCT/JP2012/075772 filed on Oct. 4, 2012 and claims benefit of Japanese Application No. 2011-260776 filed in Japan on Nov. 29, 2011, the entire contents of which are incorporated herein by this reference.

BACKGROUND OF THE INVENTION

1. Field of the Invention

The present invention relates to a polarization observation device that performs polarization observation using a polarization plate.

2. Description of the Related Art

Light incident inside a living tissue is scattered by cell nuclei, subcellular organelle, and collagen. In a case where the incident light is polarized, the polarization degree is lost by scattering, and the light eventually becomes randomly-polarized light. Scattering depends on a histological structure such as cell nuclei, subcellular organelle, and collagen. Accordingly, also a degree of depolarization due to scattering depends on the histological structure. Therefore, there is a possibility that information on the histological structure (for example, atypism or growth of tissue) can be obtained as an image by performing polarization imaging on a living tissue.

As disclosed in Japanese Patent Application Laid-Open Publication No. 2003-47588, when a beam splitter is used for obtaining a plurality of polarization images in which polarization directions are different from one another, a plurality of image pickup devices are required.

In addition, in Japanese Patent Application Laid-Open Publication No. 2010-125284, a configuration in which a polarization element array is superimposed on an image pickup device is disclosed.

SUMMARY OF THE INVENTION

A polarization observation device according to one aspect of the present invention includes: a light source section that generates illumination lights in a plurality of wavelength bands which are different from one another; a first wavelength selective polarization element that polarizes, in a first direction, a light in a first wavelength band among the illumination lights generated by the light source section or returned lights from a subject irradiated with the illumination lights; a second wavelength selective polarization element that polarizes, in a second direction different from the first direction, a light in a second wavelength band different from the first wavelength band among the illumination lights or the returned lights; an image pickup device that generates a first image pickup signal obtained by picking up an image of light polarized by the first wavelength selective polarization element and a second image pickup signal obtained by picking up an image of light polarized by the second wavelength selective polarization element; and an image processing section that receives the first image pickup signal obtained by picking up the image of the light polarized by the first wavelength selective polarization element and the second image pickup signal obtained by picking up the image of the light polarized by the second wavelength selective polarization element, compares an intensity of the first image pickup signal with an intensity of the second image pickup signal to determine which of the image pickup signals has a higher intensity, calculates a direction of the first direction and the second direction, which corresponds to the image pickup signal having the higher intensity, as a polarization direction of the subject whose image is picked up by the image pickup device, and outputs a signal for displaying information related to the polarization direction of the subject.

DETAILED DESCRIPTION OF THE PREFERRED EMBODIMENT(S)

Hereinafter, embodiments of the present invention will be described in detail with reference to drawings. A polarization observation device according to each of the present embodiments is disposed at a distal end portion of an insertion portion of an endoscope, for example.

First Embodiment

First, description will be made on an entirety of an endoscope apparatus provided with a polarization observation device according to the present invention.

Figure 1:
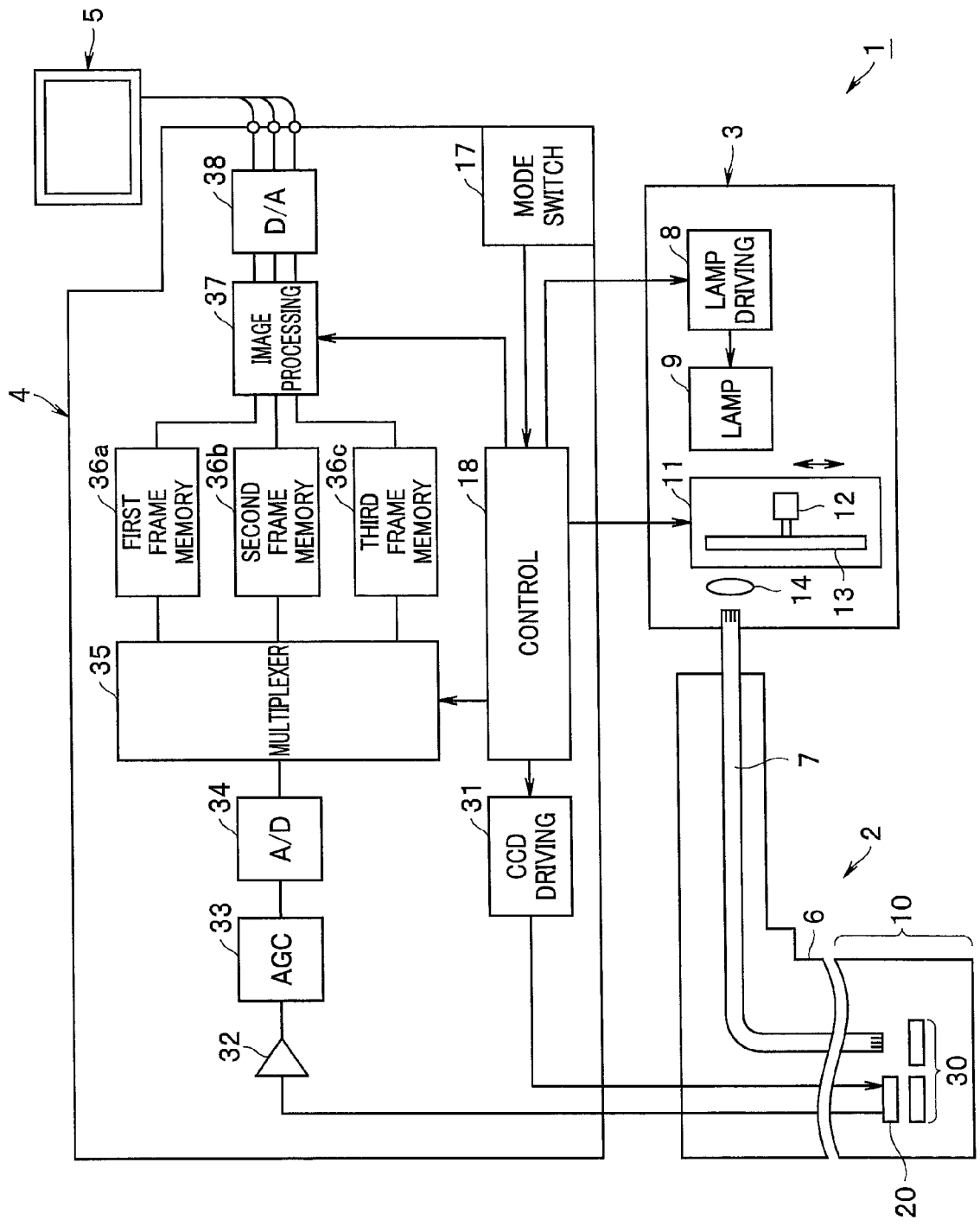
FIG. 1 is a configuration diagram illustrating an endoscope apparatus provided with a polarization observation device according to the present invention.

FIG. 1 is a configuration diagram illustrating the endoscope apparatus. An endoscope apparatus 1 includes an endoscope 2, a light source section 3, a processor 4, and a monitor 5. The endoscope 2 is constituted of an insertion portion 6, a light guide 7, and a distal end portion 10, and includes, at the distal end portion 10, a CCD 20 and a wavelength selective polarization plate 30 as a wavelength selective polarization element. Illustration of an illumination optical system and an image pickup optical system is omitted. The light source section 3 includes a lamp 9, a moving stage 11, a motor 12, a rotary filter 13, and a condensing lens 14. The processor 4 is provided with a mode switch 17, a control circuit 18, a CCD driving circuit 31, a pre-amplifier 32, an AGC circuit 33, an A/D conversion circuit 34, a multiplexer 35, frame memories 36a to 36c, an image processing circuit 37, a D/A conversion circuit 38, and the like.

In the above-described configuration, the part corresponding to the polarization observation device includes the CCD 20 as an image pickup device which photoelectrically converts returned lights from an object, a light source section 3 which generates lights in a plurality of wavelength bands different from one another, and at least one (two in FIG. 1) wavelength selective polarization plate 30 arranged between the light source section 3 and the image pickup device 20 (on an optical axis of the illumination optical system or an optical axis of the image pickup optical system) which separates a predetermined polarization component in a specific wavelength band, and which does not change the polarization component in a wavelength band other than the specific wavelength band.

First and second illumination lights in first and second wavelength bands including wavelengths $\lambda 1$, $\lambda 2$, respectively, emitted from the light source section 3 are frame-sequentially irradiated from the distal end portion 10 to an object, not shown, through the light guide 7. The illumination lights irradiated to the object may include a third illumination light in a third wavelength band in addition to the first and second illumination lights in the first and second wavelength bands.

The returned lights from the object are received by the CCD 20, and sequentially transmitted to the multiplexer 35, and a first image pickup signal based on the first illumination light, a second image pickup signal based on the second illumination light, and a third image pickup signal based on the third illumination light are once stored in first to third frame memories 36a to 36c, and thereafter polarization imaging processing is performed on the signals in the image processing circuit 37, to generate a polarization image, and further the signals are converted into analog signals to be displayed on the monitor 5. In addition, normal observation and polarization observation can be switched by the mode switch 17.

FIGS. 2A to 2D illustrate the polarization observation device according to the first embodiment of the present invention.

Figure 2A:
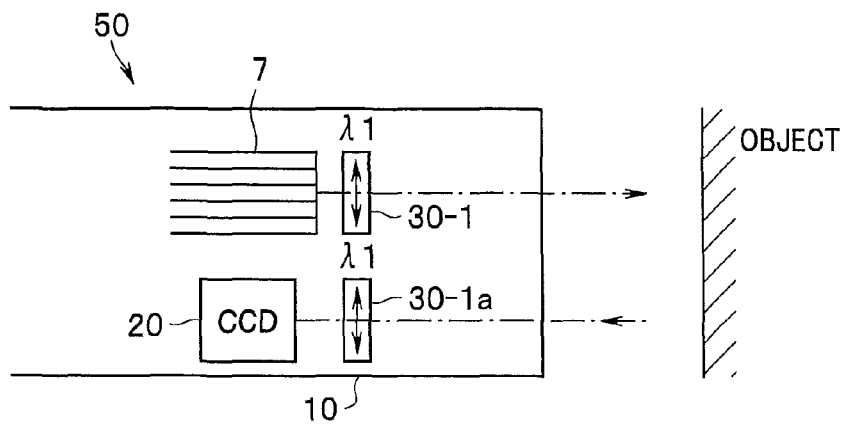
FIG. 2A illustrates parallel observation in the polarization observation device according to a first embodiment of the present invention.

FIG. 2A illustrates a parallel observation in the polarization observation device 50. The parallel observation is an observation in the case where the polarization direction of the illumination light irradiated to the object is the same as the polarization direction of the returned light received by the CCD 20. Since the light reflected on the surface of the object and a part of light scattered inside the object are received, it is possible to mainly observe the structure of the surface of the object.

A wavelength selective polarization plate 30-1 which polarizes only the light in the first wavelength band including the wavelength $\lambda 1$ is arranged on the optical axis of the illumination optical system, and a wavelength selective polarization plate 30-1a having the same characteristics as those of the wavelength selective polarization plate 30-1 is arranged on the optical axis of the image pickup optical system such that the polarization direction thereof is parallel to the polarization direction of the wavelength selective polarization plate 30-1. The light including the first wavelength band is irradiated from the light source section 3 and the returned light from the object is transmitted through the wavelength selective polarization plate 30-1a, to thereby perform the parallel observation under the light in the first wavelength band, and perform non-polarization observation under the light in a wavelength band other than the first wavelength band.

Figure 2B:
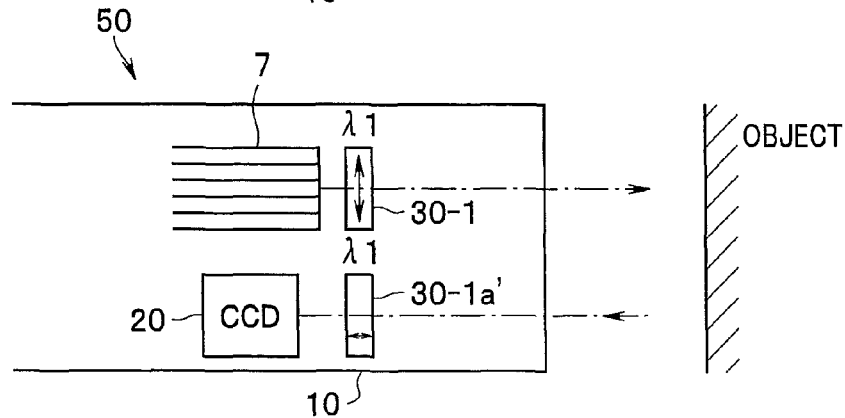
FIG. 2B illustrates crossed Nicols observation in the polarization observation device according to the first embodiment of the present invention.

FIG. 2B illustrates crossed Nicols observation in the polarization observation device 50. The crossed Nicols observation is an observation in a case where the polarization direction of the illumination light irradiated to the object is perpendicular to the polarization direction of the returned light received by the CCD 20. The light scattered inside the object is received, thereby capable of observing the structure inside the object.

The wavelength selective polarization plate 30-1 which polarizes only the light in the first wavelength band including the wavelength $\lambda 1$ is arranged on the optical axis of the illumination optical system, and the wavelength selective polarization plate 30-1a' having the same characteristics as those of the wavelength selective polarization plate 30-1 is arranged on the optical axis of the image pickup optical system such that the polarization direction thereof is perpendicular to the polarization direction of the wavelength selective polarization plate 30-1. The light including the first wavelength band is irradiated from the light source section 3 and the returned light from the object is transmitted through the wavelength selective polarization plate 30-1a', to thereby perform the crossed Nicols observation under the light in the first wavelength band, and perform non-polarization observation under the light in a wavelength band other than the first wavelength band.

Figure 2C:
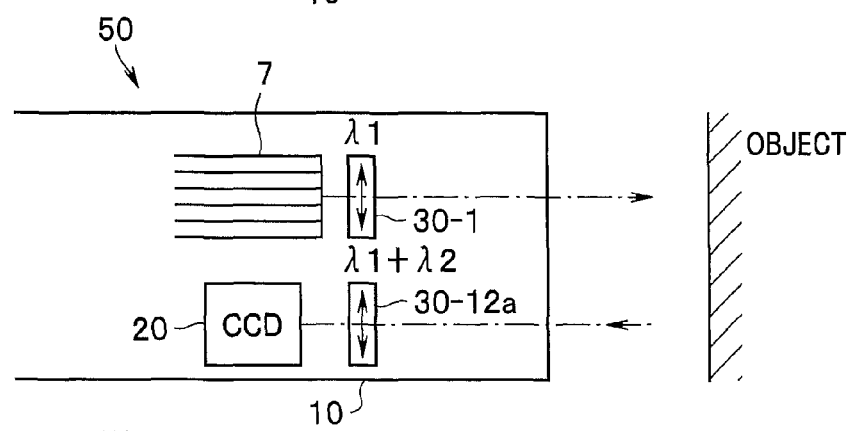
FIG. 2C illustrates an observation performed by arranging a wavelength selective polarization plate 30-12a which polarizes a light in a first wavelength band and a light in a second wavelength band in the same polarization direction as the polarization direction of a wavelength selective polarization plate 30-1, instead of a wavelength selective polarization plate 30-1a in FIG. 2A, in the polarization observation device according to the first embodiment of the present invention.

In addition, as shown in FIG. 2C, a wavelength selective polarization plate 30-12a which polarizes the light in the first wavelength band and the light in the second wavelength band in the same polarization direction as the polarization direction of the wavelength selective polarization plate 30-1 is arranged in place of the wavelength selective polarization plate 30-1a in FIG. 2A, thereby enabling the polarization observation to be performed under the light in the second wavelength band only when the CCD is brought close to the object. The polarization plate which polarizes only the light in the second wavelength is thus provided only on the image pickup side, thereby capable of obtaining a brighter polarization image compared with the case where the polarization plate is provided on both of the image pickup side and the illumination side.

Figure 2D:
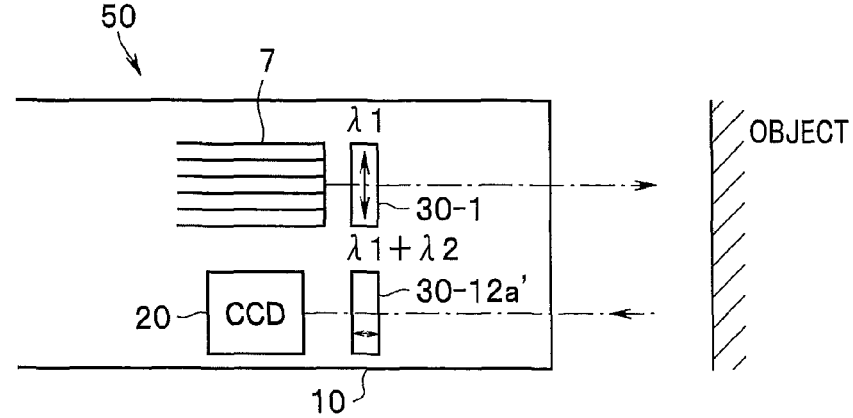
FIG. 2D illustrates an observation performed by arranging a wavelength selective polarization plate 30-12a' which polarizes the light in the first wavelength band and the light in the second wavelength band in a polarization direction perpendicular to the polarization direction of the wavelength selective polarization plate 30-1, instead of a wavelength selective polarization plate 30-1a' in FIG. 2B, in the polarization observation device according to the first embodiment of the present invention.

In addition, the same effects can be obtained even if the wavelength selective polarization plate 30-12a' which polarizes the light in the first wavelength band and the light in the second wavelength band in the polarization direction perpendicular to the polarization direction of the wavelength selective polarization plate 30-1, as shown in FIG. 2D.

Figure 3:
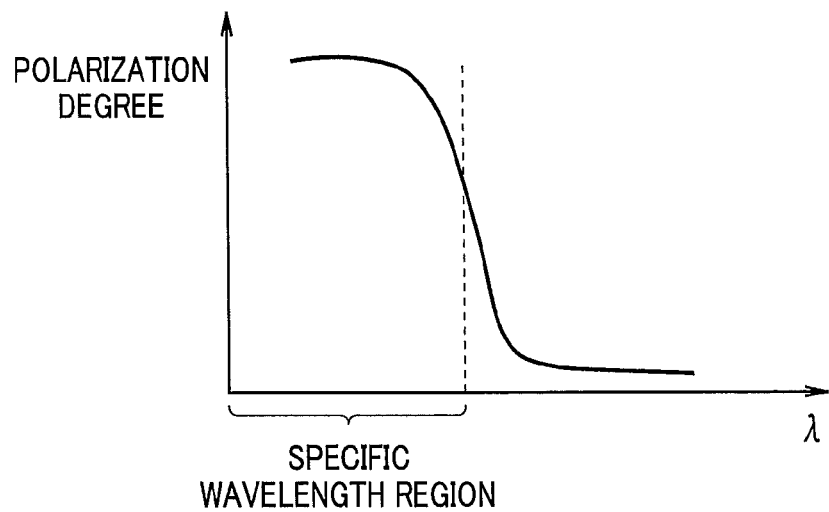
FIG. 3 illustrates a characteristic example of a wavelength selective polarization plate according to the present invention.

Note that, in the present invention, the wavelength selective polarization plate which polarizes only the light in a specific wavelength band is not necessarily required to completely polarize the light in the specific wavelength band or not necessarily required to completely maintain non-polarization state of the light in a wavelength band other than the specific wavelength band. For example, as shown in FIG. 3, the wavelength selective polarization plate may have characteristics in which the polarization degree does not show a rapid change in the border between the specific wavelength band and the wavelength band other than the specific wavelength band.

Second Embodiment

Figure 4:
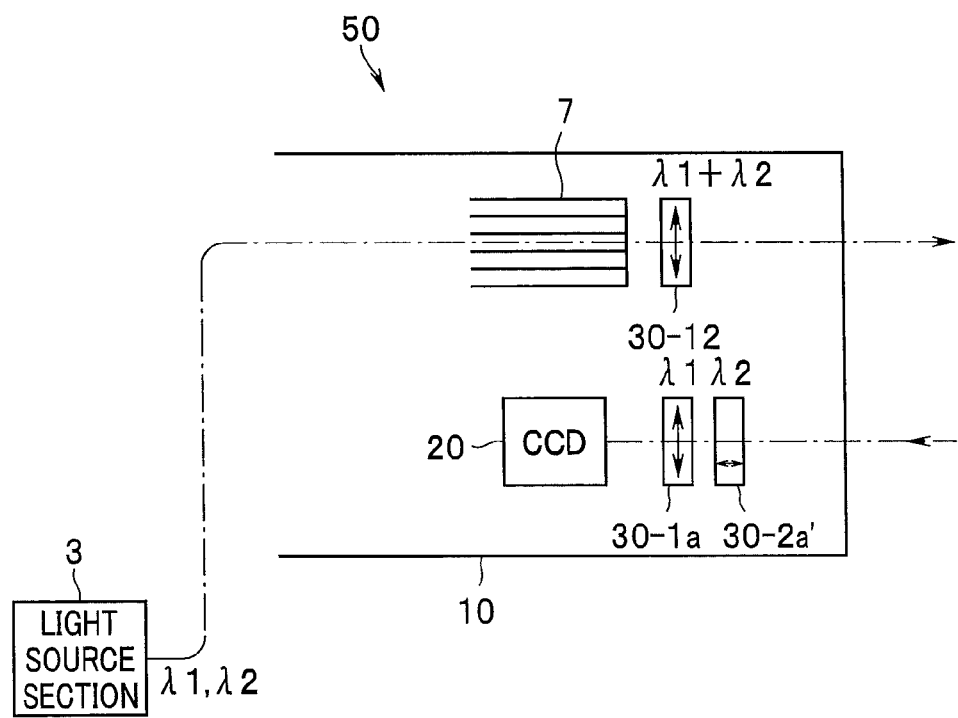
FIG. 4 illustrates a polarization observation device according to a second embodiment of the present invention.

FIG. 4 illustrates a polarization observation device according to a second embodiment of the present invention.

The polarization observation device 50 includes the CCD 20 which photoelectrically converts returned lights from an object not shown, the light source section 3, and three wavelength selective polarization plates 30 arranged between the light source section 3 and the CCD 20 (on the optical axis of the illumination optical system and the optical axis of the image pickup optical system). The light source section 3 generates the first and second illumination lights in the first and second wavelength bands including the wavelengths $\lambda 1$, $\lambda 2$, respectively.

The first illumination light and the second illumination light emitted from the light source section 3 are frame-sequentially irradiated from the distal end portion 10 to the object using the light guide 7. The illumination lights may include illumination light in the third wavelength band different from the first and second wavelength bands.

The wavelength selective polarization plates 30 are constituted of a wavelength selective polarization plate 30-12 arranged on the optical axis of the illumination optical system and wavelength selective polarization plates 30-1a, 30-2a' arranged on the optical axis of the image pickup optical system. The wavelength selective polarization plate 30-12 polarizes the light in the first wavelength band and the light in the second wavelength band in a first polarization direction. The wavelength selective polarization plate 30-1a polarizes the light in the first wavelength band in the first polarization direction, and the wavelength selective polarization plate 30-2a' polarizes the light in the second wavelength band in a second polarization direction perpendicular to the first polarization direction.

According to such a configuration, the parallel observation is performed under the light in the first wavelength band, and the crossed Nicols observation is performed under the light in the second wavelength band, thereby capable of obtaining two kinds of polarization images at the same time.

In addition, the non-polarization observation is possible without reducing the observation light amount at all. It is also possible to combine with other special light technology such as narrow-band light observation.

Figure 5:
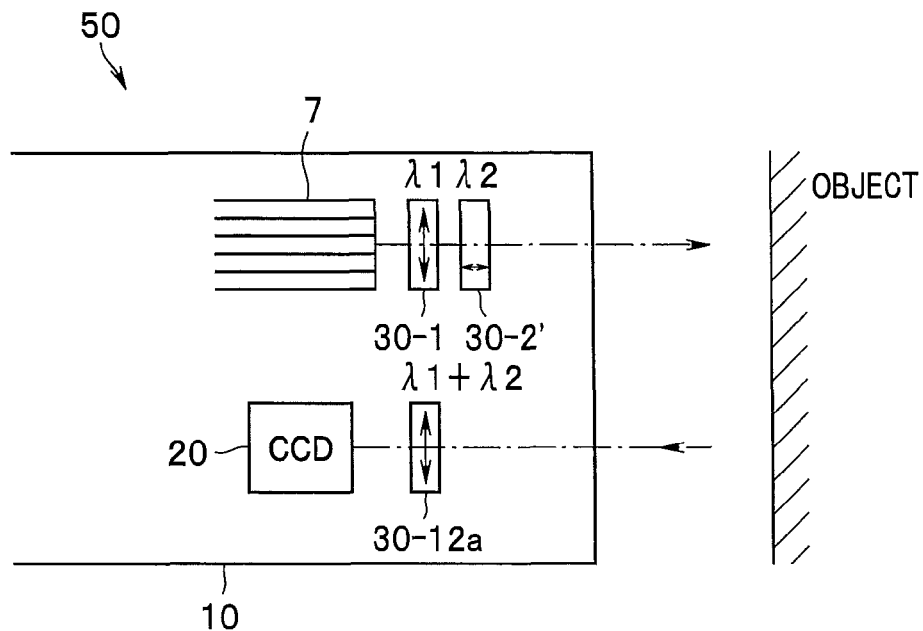
FIG. 5 illustrates a modified example according to the second embodiment of the present invention.

Note that, as shown in FIG. 5, arrangement of the polarization plates on the illumination side and the image pickup side may be reversed from that shown in FIG. 4.

According to the second embodiment, the polarization direction of the wavelength selective polarization plate arranged on the illumination optical system side is coincided with the polarization direction of the wavelength selective polarization plate arranged on the image pickup optical system side, thereby capable of observing the structure of the surface of the object. Furthermore, the polarization direction of the wavelength selective polarization plate arranged on the illumination optical system side is made different from (for example, perpendicular to) the polarization direction of the wavelength selective polarization plate arranged on the image pickup optical system, thereby capable of observing information inside the living body.

Third Embodiment

Figure 6:
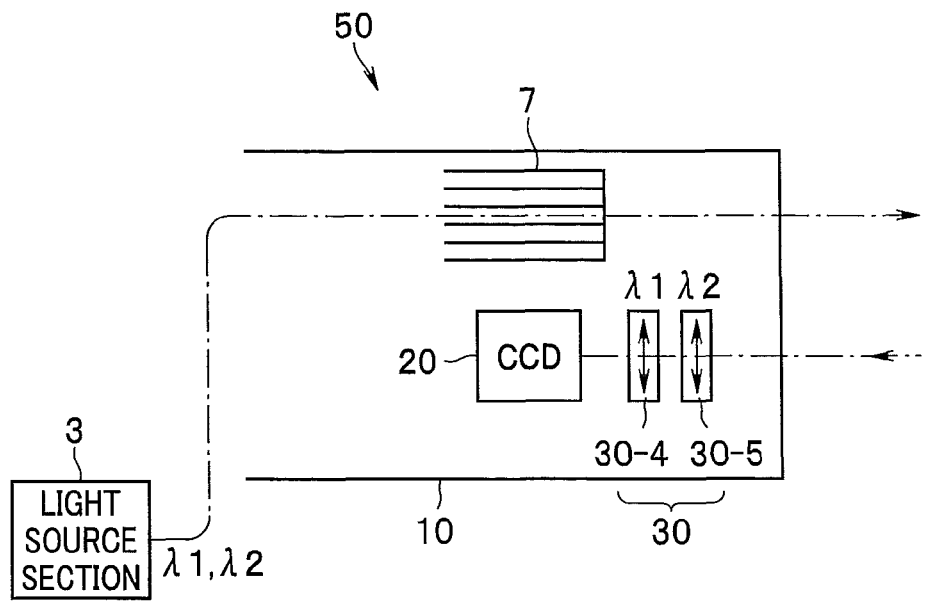
FIG. 6 illustrates a polarization observation device according to a third embodiment of the present invention.

FIG. 6 illustrates a polarization observation device according to a third embodiment of the present invention.

The polarization observation device 50 includes the CCD 20 which photoelectrically converts returned lights from the object, the light source section 3, and two wavelength selective polarization plates 30, which separates predetermined polarization components of the lights in the first and second wavelength bands including the wavelengths $\lambda 1$, $\lambda 2$, and which does not change the polarization components of the lights in the wavelength bands other than the specific wavelength bands, are provided between the light source section 3 and the CCD 20 (on the optical axis of the image pickup optical system in FIG. 6).

The first and second illumination lights in the first and second wavelength bands including the wavelengths $\lambda 1$, $\lambda 2$, respectively, are frame-sequentially emitted from the light source section 3, to be sequentially irradiated from the distal end portion 10 to the object through the light guide 7. The illumination lights frame-sequentially irradiated from the light source section 3 to the object may include the third illumination light in the third wavelength band different from the first and second wavelength bands.

The wavelength selective polarization plates 30 are constituted of a wavelength selective polarization plate 30-4 which polarizes the first illumination light in the first polarization direction and a wavelength selective polarization plate 30-5 which polarizes the second illumination light in the second polarization direction.

According to such a configuration, a plurality of images in which the polarization components are different from one another, a polarization image, and a non-polarization image can be obtained at the same time.

The wavelength selective polarization plate 30-4 which polarizes only the light in the first wavelength band, and the wavelength selective polarization plate 30-5 which has a transmission axis perpendicular to that of the wavelength selective polarization plate 30-4 and which polarizes only the light in the second wavelength band are arranged on the optical axis of the image pickup optical system, the light in the first wavelength band including the wavelength $\lambda 1$, the light in the second wavelength band including the wavelength $\lambda 2$, and the light in the third wavelength band different from the first wavelength band and the second wavelength band are irradiated from the light source section 3, and the returned lights from the object transmit the wavelength selective polarization plates 30-4, 30-5, thereby enabling the non-polarization observation to be performed under the light in the third wavelength band, and enabling the polarization observation in which the polarization components are different from each other by 90 degrees to be performed under the light in the first wavelength band and the light in the second wavelength band. Inter-image calculation is performed on corresponding images having different polarization components (subtract the polarization image in the second wavelength band from the polarization image in the first wavelength band), thereby causing a polarization difference image to be outputted.

Figure 7:
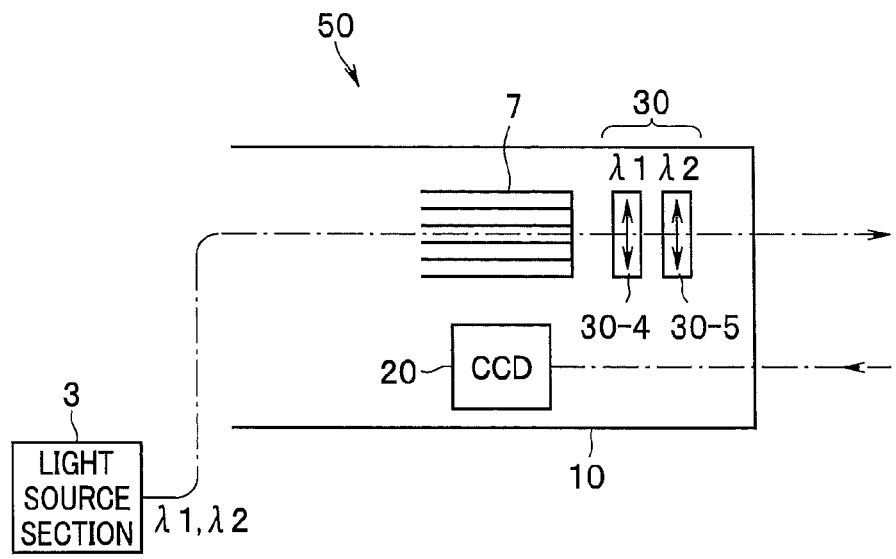
FIG. 7 illustrates a modified example according to the third embodiment of the present invention.

Note that, as shown in FIG. 7, the same effects can be obtained also in the case where the wavelength selective polarization plates 30-4, 30-5 of the present embodiment are arranged on the optical axis of the illumination optical system.

Furthermore, the wavelength selective polarization plates may be arranged on both of the illumination side and the image pickup side, and the number of the wavelength selective polarization plates is not limited to four.

When the object is a living tissue, the layer in which the polarization characteristics are exhibited is located at the depth of hundreds of μm from the surface layer. Therefore, it is possible to effectively obtain the polarization characteristics of the living body by optimizing the depth of penetration of the light using the wavelengths.

The layer in which the living tissue exhibits the polarization characteristics is considered to be a fiber tissue, and it is known that the polarization directions are aligned to a certain constant direction by the fiber tissue. That is, when the polarization directions aligned by the fiber tissue become parallel to the transmission axes of the polarization plates, the light amount of the received light increases, and when the polarization directions become vertical to the transmission axes, the light amount of the received light decreases.

In addition, since the returned lights from a lesion tissue are greatly affected by scattering, the returned lights do not reach the fiber tissue, or polarized lights, directions of which are aligned, are randomized to be detected. However, since the returned lights from a normal tissue are less affected by scattering, the polarized lights are detected with the polarization characteristics of the living tissue maintained.

On the basis of the above, it is possible to emphasize the contrast of the boundary between the normal tissue and the lesion tissue by positively receiving the polarized lights with the polarization characteristics from the normal tissue maintained, or by positively limiting the receiving of the polarized lights from the normal tissue.

Since the two polarization images, the polarization components of which are different from each other by 90 degrees, are respectively an image obtained by positively receiving the polarized lights with the polarization characteristics from the normal tissue maintained and an image obtained by positively limiting the receiving of the polarized lights from the normal tissue, it is possible to further emphasize the contrast of the boundary between the normal portion and the tumor portion by performing subtraction on pixel values at corresponding pixels. In other words, in the tumor portion of the living tissue, regarding the two polarization images in which polarization components are different from each other by 90 degrees, there is little difference between the image obtained by positively receiving the polarized lights with the polarization characteristics from the tissue maintained and the image obtained by positively limiting the receiving of the polarized lights from the tissue. The difference is large in the normal portion.

A plurality of wavelength selective polarization plates having transmission axes whose directions are different from one another are disposed on an optical axis, and light intensities are compared at corresponding pixels in the images created by the lights polarized with the respective wavelengths, and the direction of the transmission axis of the wavelength selective polarization plate through which a polarization image including the pixel having the highest value of the light intensity is obtained is specified as a polarization direction of the light received at each of the pixels.

For example, by constantly performing processing (of subtracting a polarization image obtained by rotating the polarization direction by 90 degrees from the polarization image in which the polarization direction is specified), the normal portion of the object is always displayed more brightly and the lesion portion is displayed more darkly, irrespective of the type of the observation system, thereby emphasizing the contrast of the boundary between the normal portion and the lesion portion. Therefore, when there is little difference among the light intensities at corresponding pixels in the images created by the lights polarized with the respective wavelengths, the polarization degree is low and the portion is suspected as a lesion tissue. On the other hand, the difference is large, the polarization degree is high and the polarization characteristics in the living tissue are observed, thereby capable of evaluating that the portion is a normal tissue. If the difference among the corresponding pixels is displayed with a color map or the like, for example, it could be possible to differential diagnosis between the normal tissue and the lesion tissue. Next, description will be made on a configuration in which wavelength selective polarization plates 30-4, 30-5, and 30-6, which only polarize the light of the wavelength $\lambda 1$ (0 degree), the light of the wavelength $\lambda 2$ (45 degrees) and the light of the wavelength $\lambda 3$ (90 degrees), respectively, are disposed on the optical axis of the image pickup optical system.

The light intensities at the corresponding pixels in the polarization images created by the lights transmitting the wavelength selective polarization plates 30-4, 30-5, and 30-6 are compared with one another, and the direction of the transmission axis of the polarization plate through which the polarization image including the pixel having the highest value of light intensity is obtained is specified as the polarization direction of the light received at each of the pixels.

For example, when the light intensity at a certain pixel in the image created by the light polarized with the wavelength $\lambda 2$ shows a higher value compared with the light intensities at corresponding pixels in the images created by the lights polarized with the wavelengths $\lambda 1$, $\lambda 3$, the polarization direction of the light received at the certain pixel is the direction of the transmission axis of the polarization plate which transmits the light of the wavelength $\lambda 2$.

Figure 8:
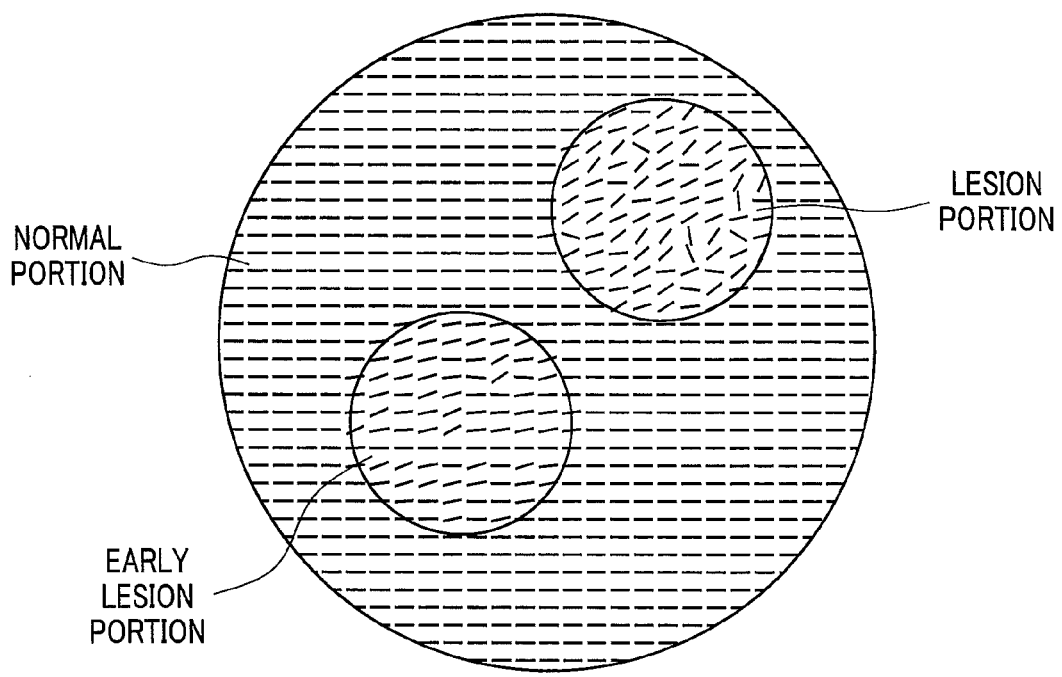
FIG. 8 illustrates a state where polarization observation is performed on a phantom by using the polarization observation device according to the present invention.

For example, a value is calculated (by subtracting the polarization image obtained by rotating the polarization direction by 90 degrees from the polarization image in which the polarization direction is specified) at each pixel, and the value is shown with the color map as shown in FIG. 8, thereby enabling quantitative evaluation of the polarization characteristics of the living tissue and scattering characteristics of the tissue in the more superficial layer than the layer having the polarization characteristics in the living tissue. In addition, diagnosis of the invasion depth at the lesion portion is also possible.

FIG. 8 illustrates a state in which polarization observation is performed on a phantom as a mimic specimen of a living body using the polarization observation device according to the present invention.

The phantom has a normal portion and lesion portion formed in a mimicked manner by using silicone material which is supposed to be a living tissue. FIG. 8 illustrates the state where the phantom is photographed using the polarization observation device and shown with the color map. The normal portion, the lesion portion, and the early lesion portion are displayed in green color, yellow color and greenish yellow color, respectively. The directions of the fibers in the fiber tissue are aligned with regularity in the normal portion. In contrast, the directions of the fibers in the fiber tissue are randomly aligned in the lesion portion. In the early lesion portion, the directions of the fibers are a little out of alignment. Normally, the normal portion has a low grade, in other words, the normal portion is a portion where the tissue has a polarity, on the other hand, the lesion portion has a high grade, in other words, the lesion portion is a portion where the tissue does not have a polarity.

Note that the directions of the polarized lights at the respective portions shown in FIG. 8 may be displayed with arrows.

Figure 9:
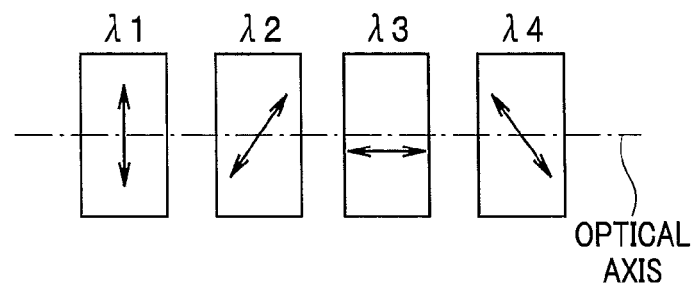
FIG. 9 illustrates an alignment example of the wavelength selective polarization plates in the polarization observation device according to the present invention.

FIG. 9 illustrates an alignment example of the wavelength selective polarization plates in the polarization observation device according to the present invention. Four wavelength selective polarization plates which polarize lights of four wavelengths $\lambda 1$, $\lambda 2$, $\lambda 3$, and $\lambda 4$, respectively, in four polarization directions are arranged so as to be aligned on the optical axis. Illumination lights of first to fourth wavelength bands including the wavelengths $\lambda 1$, $\lambda 2$, $\lambda 3$, and $\lambda 4$, respectively, are emitted from a light source section, not shown, to be irradiated to an object through the four wavelength selective polarization plates. The lights of the wavelengths $\lambda 1$, $\lambda 2$, $\lambda 3$, and $\lambda 4$ are polarized by the four wavelength selective polarization plates in the respective polarization directions, to be irradiated to the object. The four wavelength selective polarization plates may be arranged in the image pickup optical system.

The number of the wavelength selective polarization plates is not limited to four. In the structural meaning, it is preferable to use the plurality of wavelength selective polarization plates which are unified by joining.

Figure 10:
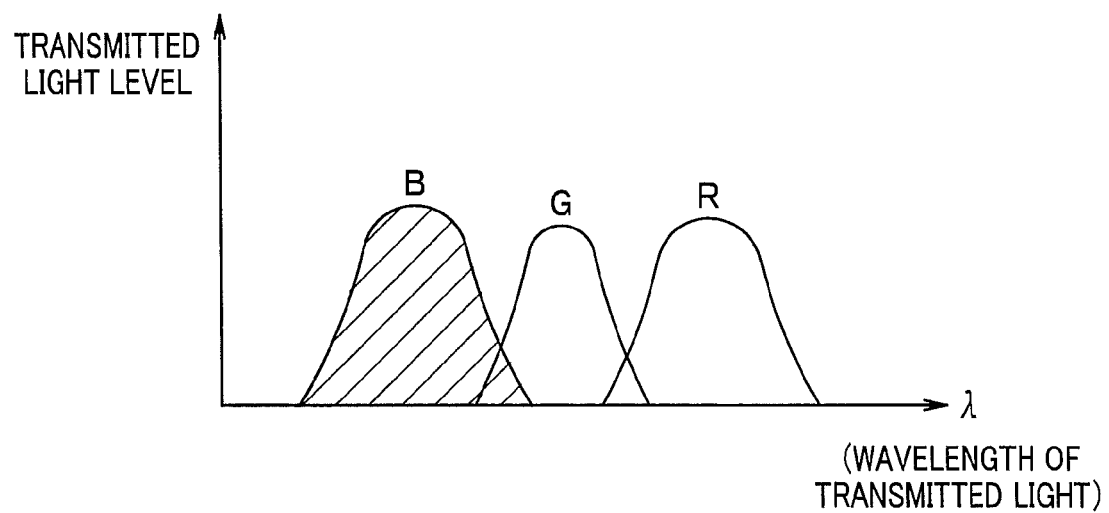
FIG. 10 illustrates an example of wavelength bands used in the polarization observation device according to the present invention.
Figure 11:
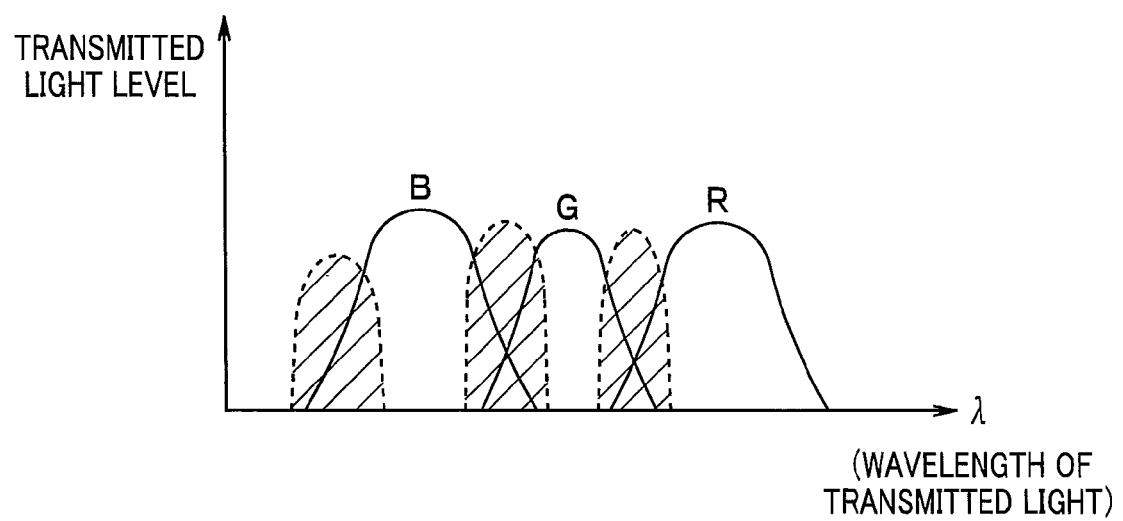
FIG. 11 illustrates another example of wavelength bands used in the polarization observation device according to the present invention.

FIGS. 10 and 11 each illustrates an example of wavelength bands to be used in the polarization observation device according to the present invention.

For example, as shown in FIG. 10, it is possible to perform polarization observation in which only the light having B components is polarized in a specific polarization direction, with a simple configuration. It is needless to say that such a polarization observation and non-polarization observation with normal B, G, and R components can be performed at the same time.

In addition, as shown in FIG. 11, it is possible to obtain the polarization image of the light components shown with hatchings between B and G, G and R, and R and B bands in the normal observation. The three light components shown with the hatchings in FIG. 11 enable the polarization observation to be performed with the wavelengths close to the B, G, and R components in the normal observation. The illumination lights from the light source required for the polarization observation shown in FIG. 10 and FIG. 11 are generated by a combination of the rotary filter which has the respective transmission bands as shown in FIGS. 10 and 11, and white light source.

Note that the present invention is not limited to the above-described embodiments, and various changes, modifications, and the like are possible in a range without changing the gist of the present invention.

For example, description has been made based on the frame-sequential method as the image pickup method. However, the present invention can be applied to a simultaneous type system.

What is claimed is:

1. A polarization observation device comprising:
a light source section that generates illumination lights in a plurality of wavelength bands which are different from one another;
a first wavelength selective polarization element that polarizes, in a first direction, a light in a first wavelength band among the illumination lights generated by the light source section or returned lights from a subject irradiated with the illumination lights;
a second wavelength selective polarization element that polarizes, in a second direction different from the first direction, a light in a second wavelength band different from the first wavelength band among the illumination lights or the returned lights;
an image pickup device that generates a first image pickup signal obtained by picking up an image of light polarized by the first wavelength selective polarization element and a second image pickup signal obtained by picking up an image of light polarized by the second wavelength selective polarization element; and
an image processing section that receives the first image pickup signal obtained by picking up the image of the light polarized by the first wavelength selective polarization element and the second image pickup signal obtained by picking up the image of the light polarized by the second wavelength selective polarization element, compares an intensity of the first image pickup signal with an intensity of the second image pickup signal to determine which of the image pickup signals has a higher intensity, calculates a direction of the first direction and the second direction, which corresponds to the image pickup signal having the higher intensity, as a polarization direction of the subject whose image is picked up by the image pickup device, performs processing of subtracting a polarization image obtained by rotating the polarization direction by 90 degrees from a polarization image in which the polarization direction is specified as a polarization image with the higher intensity, and thereby outputs a signal for displaying information related to the polarization direction of the subject.

2. The polarization observation device according to claim 1, wherein
the image pickup device is constituted of a plurality of pixels, and
the image processing section compares the intensity of the first image pickup signal with the intensity of the second image pickup signal for each of the pixels of the image pickup device, and calculates the polarization direction of the subject for each of the pixels.

3. The polarization observation device according to claim 2, wherein
the first wavelength selective polarization element transmits a polarization component in the first direction with respect to the light in the first wavelength band,
the second wavelength selective polarization element transmits a polarization component in the second direction with respect to the light in the second wavelength band, and
the first wavelength selective polarization element and the second wavelength selective polarization element are provided on an optical path from the light source section up to the image pickup device.

* * * * *